US00PP13220P2

(12) United States Plant Patent
Marchini

(10) Patent No.: US PP13,220 P2
(45) Date of Patent: Nov. 12, 2002

(54) ALMOND TREE NAMED 'MARCHINI'

(76) Inventor: Joseph C. Marchini, 11986 E. Le Grand Rd., Le Grand, CA (US) 95333

( * ) Notice: Subject to any disclaimer, the term of this patent is extended or adjusted under 35 U.S.C. 154(b) by 0 days.

(21) Appl. No.: 09/874,024

(22) Filed: Jun. 6, 2001

(51) Int. Cl.[7] ..... A01H 5/00
(52) U.S. Cl. ..... Plt./155
(58) Field of Search ..... Plt./155

*Primary Examiner*—Bruce R. Campell
*Assistant Examiner*—Susan B. McCormick

(57) ABSTRACT

The present invention relates to an almond tree, botanical classification *Prunus dulcis* cultivar 'MARCHINI', and more particularly to a new and distinct variety broadly characterized by a large size, vigorous, hardy, self-sterile, productive and regular bearing tree whose nuts mature under the ecological conditions described approximately the last week in August. The nut is medium in size and is enclosed by a soft, open shell that is easily removed by hand or by machanical shellers. The shelled nut may be marketed as a whole, blanched, sliced or diced product. The inshell nut is very suitable as a roasted and salted product.

1 Drawing Sheet

BOTANICAL CLASSIFICATION

*Prunus dulcis* cultivar 'MARCHINI'.

BACKGROUND OF THE VARIETY

The present invention relates to a new and distinct variety of almond tree, *Prunus dulcis,* which has been denominated varietally as "MARCHINI". The variety was discovered by me in 1962 as a chance seedling in a cultivated area of my property located at 1435 South Cook Street in the town of Le Grand, Calif., in Merced County (San Joaquin Valley). This seedling was one of many to sprout following the removal of a 'Nonpareil' (unpatented), 'Davey' (unpatented), and 'Neplus' (unpatented) planting. A row of these seedlings was purposely left along the edge of the property to form a natural barrier, and this particular tree stood out during the first few years for heavy production. Subsequent to the discovery of the present variety of almond tree, I asexually reproduced it by budding and grafting in my almond orchard located one mile from the discovery site, and such reproduction of plant and fruit characteristics were true to the original plant in all respects. Over the years further reproductions by budding were made in my orchard located at 11986 East Le Grand Road, Le Grand, Calif., for continued testing and evaluation purposes. These reproductions of the variety included the use of 'Nemaguard' (unpatented) and 'Lovell' (unpatented) rootstocks upon which the present variety was compatible and true to type.

I originally tested and selected the present variety because of its heavy production and its potential to pollinate 'Nonpareil' (unpatented), blooming about 3 days later than 'Nonpareil'. With the emergence of the 'Carmel' (U.S. Plant Pat. No. 2,641) as a prominent commercial variety in California, the value of the present variety as a pollinator and co-planter with both 'Nonpareil' and 'Carmel' became substantial. During the last few years the demand for an almond suitable for marketing as a roasted, salted, inshell product has substantially increased. The present variety is perfectly suited for this purpose, as it has a very soft shell for easy hand removal and an open shell to facilitate the salting process.

The present almond variety is most similar to 'Nonpareil' (unpatented) by being a relatively early blooming variety that produces light colored nuts enclosed in a soft shell, but is distinguished therefrom and an improvement thereon by having a smaller nut, by harvesting one week later, by being more productive, by appearing to be free of bud-failure, and by being interfertile with both 'Nonpareil' and 'Carmel' (U.S. Plant Pat. No. 2,641).

DRAWING

The accompanying color photograph exhibits nuts in hull, nuts out of hull, kernels out of shell, and leaves, all typical of the instant variety.

POMOLOGICAL CHARACTERISTICS

Referring now more specifically to the pomological characteristics of this new and distinct variety of almond tree, the following has been observed under the ecological conditions prevaling near Le Grand, Merced County (San Joaquin Valley), Calif., and was developed at the harvest stage on Aug. 25, 2001. All major color code designations are by reference to the Inter-Society Color Council, National Bureau of Standards. Common color names are also used occasionally.

TREE

Size: Large, reaching a height of 12' [3.66 m.] after three growing seasons and 24' [7.32 m.] after fourteen growing seasons when grown on Nemaguard Rootstock (unpatented).

Vigor: Vigorous, responding typically to irrigation and fertilization. The plant should be grown on a standard commercial rootstock for production purposes.

Growth: Upright and dense.

Form: Vase formed and spreading.

Hardiness: Hardy with respect to central California winters.

Production: Very productive.

Fertility: Self-sterile, must be cross pollinated by other almond varieties, including 'Nonpareil' (unpatented), 'Carmel' (U.S. Plant Pat. No. 2,641) and 'Texas' (unpatented).

Bearing: Regular bearer with no significant alternate bearing observed.

Date of harvest: Aug. 25, 2000, 1 week after 'Nonpareil'.

Trunk:

*Size*.—Medium, reaching a maximum diameter of 6" [152 mm.] after three growing seasons and a maximum diameter of 13.5" [343 mm.] after fourteen growing seasons when grown on Nemaguard Rootstock.

*Texture*.—Somewhat shaggy.

*Bark color*.—Grayish brown [61. gy.Br].

*Lenticels*.—Approximately 16 per square inch. Color: Strong yellowish brown [74. s.yBr]. Average Size: ¼" [6.4 mm.].

Branches:

*Size*.—Average diameter is 7" [178 mm.] measured 12" above the crotch on the 14 year old tree, typical of *Prunus dulcis*.

*Texture*.—Smooth on 1st year wood, increasing roughness with age and accumulation of lenticels.

*Color*.—1st Year Wood Topside: Moderate reddish brown [43. m.rBr]. 1st Year Wood Underside: Brilliant yellow green [116. brill.YG]. Older Wood: Moderate brown [58. m.Br].

*Lenticels*.—Approximately 80 per square inch. Color: Strong yellowish brown [74. s.yBr]. Average Size: ⅛" to 3⁄16" [3.2–4.8 mm.].

Leaves:

*Size*.—Medium. Average Length: 3¼" [82.6 mm.]. Average Width: 1⅛" [28.6 mm.].

*Thickness*.—Medium.

*Form*.—Elliptical.

*Apex*.—Acuminate.

*Base*.—Acute.

*Surface*.—Smooth.

*Color*.—Dorsal Surface: Dark olive green [126. d.OlG]. Ventral Surface: Grayish green [150. gy.G].

*Margin*.—Finely serrate.

*Venation*.—Pinnately net veined.

*Vein color*.—Light yellow green [119. l.YG].

*Petiole*.—Average Length: 1" [25.4 mm.]. Average Thickness: 1⁄16" [1.6 mm.]. Color: Light yellow green [119. l.YG].

*Stipules*.—Few, usually 2 per leaf. Average Length: 3⁄16" [4.8 mm.].

*Glands*.—Numbers: 2 to 4 per leaf. Position: Alternately positioned on the petiole and the base of blade. Size: Small. Form: Globose. Color: Grayish reddish brown [46. gy.rBr].

*Leaf buds*.—Pointed.

Flower buds:

*Hardiness*.—Hardy, with respect to central California winters.

*Diameter*.—Typically 5⁄16" [7.9 mm.] 1 week before bloom.

*Length*.—Typically 9⁄16" [14.3 mm.] 1 week before bloom.

*Form*.—Conic, not appressed.

*Surface*.—Pubescent.

*Color*.—White [263. White].

Flowers: Perfect, complete, perigynous, usually a single pistil, typically thirty or more stamens, five sepals and petal locations alternately positioned.

*Type*.—Showy.

*Average flower diameter*.—2" [50.8 mm.].

*Number of petals*.—Usually five, very few doubles.

*Petal shape*.—Obovate.

*Petal apex*.—Primarily obtuse with a few emarginate.

*Petal base*.—Typically forms a 120° angle.

*Petal margin*.—Undulate.

*Average petal width*.—⅝" [15.9 mm.].

*Average petal length*.—⅞" [22.2 mm.].

*Petal color*.—White [263. White].

*Anther color*.—Brilliant yellow [83. brill.Y].

*Stigma color*.—Light yellow green [119. l.YG].

*Average sepal width*.—3⁄16 [4.8 mm.].

*Average sepal length*.—¼" [6.4 mm.].

*Sepal color*.—Dark grayish red [20. d.gy.R].

*Average pistil length*.—⅝" [15.9 mm.].

*Average stamen length*.—7⁄16" [11.1 m.].

*Fragrance*.—Moderate.

*Blooming period*.—Somewhat early, or about 3 days later than 'Nonpareil' (unpatented).

*Onset of bloom*.—One percent on Feb. 18, 2001.

*Date of full bloom*.—Feb. 28, 2001.

*Duration of bloom*.—One to two weeks, dependent on ambient temperature.

*Number per cluster*.—1 to 5, average 3.

HULL

Outer surface: Smooth at hull split, roughens upon drying, pubescent.

Form: Uniform, symmetrical.

*Longitudinal section form*.—Oval.

Average thickness: 3⁄32" to ⅛" [2.4–3.2 mm.] when dry.

Flesh: Tough.

Suture: A sharp crack prior to splitting.

External color: Grayish yellow green [122. gy.YG] at hull split turning to Grayish yellowish brown [80. gy.yBr] upon drying.

Dehiscence: Opens freely.

Splitting: Complete along suture.

Adherence: Hulls are easily removed from nuts by mechanical hullers.

Density: Hulls are tough, stay intact, and can be readily skimmed by mechanical classifiers during hulling and shelling processes.

Nut cavity: Oval.

*Surface*.—Rough.

*Color when first opened*.—Light orange yellow [70. l.OY].

*Color when dry*.—Dark orange yellow [72. d.OY].

NUT

Size:

*Average length*.—1 3⁄16" [30.2 mm.].

*Average width*.—13⁄16" [20.6 mm.].

*Average thickness*.—⅝" [15.9 mm.].

*Average weight*.—16.9 nuts per ounce [1.68 grams per nut].

Form: Oval.

Shell:

*Color*.—Light grayish yellowish brown [79. l.gy.yBr].

*Average wall thickness*.—1⁄16" [1.6 mm.].

*Pits*.—Small, numerous.

*Shell*.—Thin and brittle, many having an open crack along the dorsal fin.

Base: Straight.

Apex: Acute, average 80 degrees.

Stem: Medium.
*Average length.*—5/16" [7.9 mm.].
*Average diameter.*—3/16" [4.8 mm.].
Wing: Thin, somewhat more extended toward apex.
*Average protrusion.*—1/8" [3.2 mm.].
Inner surface: Smooth.
*Color.*—Light yellowish brown [76. l.yBr].

KERNEL

Size: Medium.
*Average length.*—15/16" [23.8 mm.].
*Average width.*—9/16" [14.3 mm.].
*Average thickness.*—5/16" [7.9 mm.].
*Average weight.*—24.0 nuts per ounce [1.18 grams per nut].
Form: Symmetrical.
*Longitudinal section form.*—Ovate.
*Transverse section form.*—Oval.
Base: Straight.
Apex: Acute, average 90 degrees.
Surface: Slightly wrinkled, very slight pubescence.
*Skin color.*—Strong yellowish brown [74. s.yBr].
*Pellicle color.*—Grayish brown [61. gy.Br].
*Veins.*—Numerous moderate yellowish brown [77. m.yBr] veins extending longitudinally from the pellicle to the apex with some branching.
Number of doubles: Moderate, about 10 percent.
Number of defective kernels: Very few on most years.
Flavor: Mild and slightly sweet.
Astringency: None.
Quality: Good.
Viable: Yes.
Blanchable: Yes.
Percentage of kernel to nut: 70 percent when fully dry.

USE

The present variety may be processed and marketed as a whole, blanched, sliced, or diced product. It has the additional quality of being an excellent natural, salted, or roasted inshell product due to its soft shell that facilitates hand shelling, competing as a concessionary product with the peanut.

CULTURAL CHARACTERISTICS

Resistance to insects: Susceptible to worm and insect damage due to its open shell.
Susceptibility to bud-failure: None observed.
Resistance to other diseases: No unusual susceptibilities noted.
Susceptibility to frost: No unusual susceptibility noted.

Although the new variety of almond tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of almond tree, substantially as illustrated and described, which is most similar to 'Nonpareil' (unpatented) by being a relatively early blooming variety that produces light colored nuts enclosed in a soft shell, but is distinguished therefrom and an improvement thereon by having a smaller nut, by harvesting one week later, by being more productive, by appearing to be free of bud-failure, and by being interfertile with both 'Nonpareil' and 'Carmel' (U.S. Plant Pat. No. 2,641).

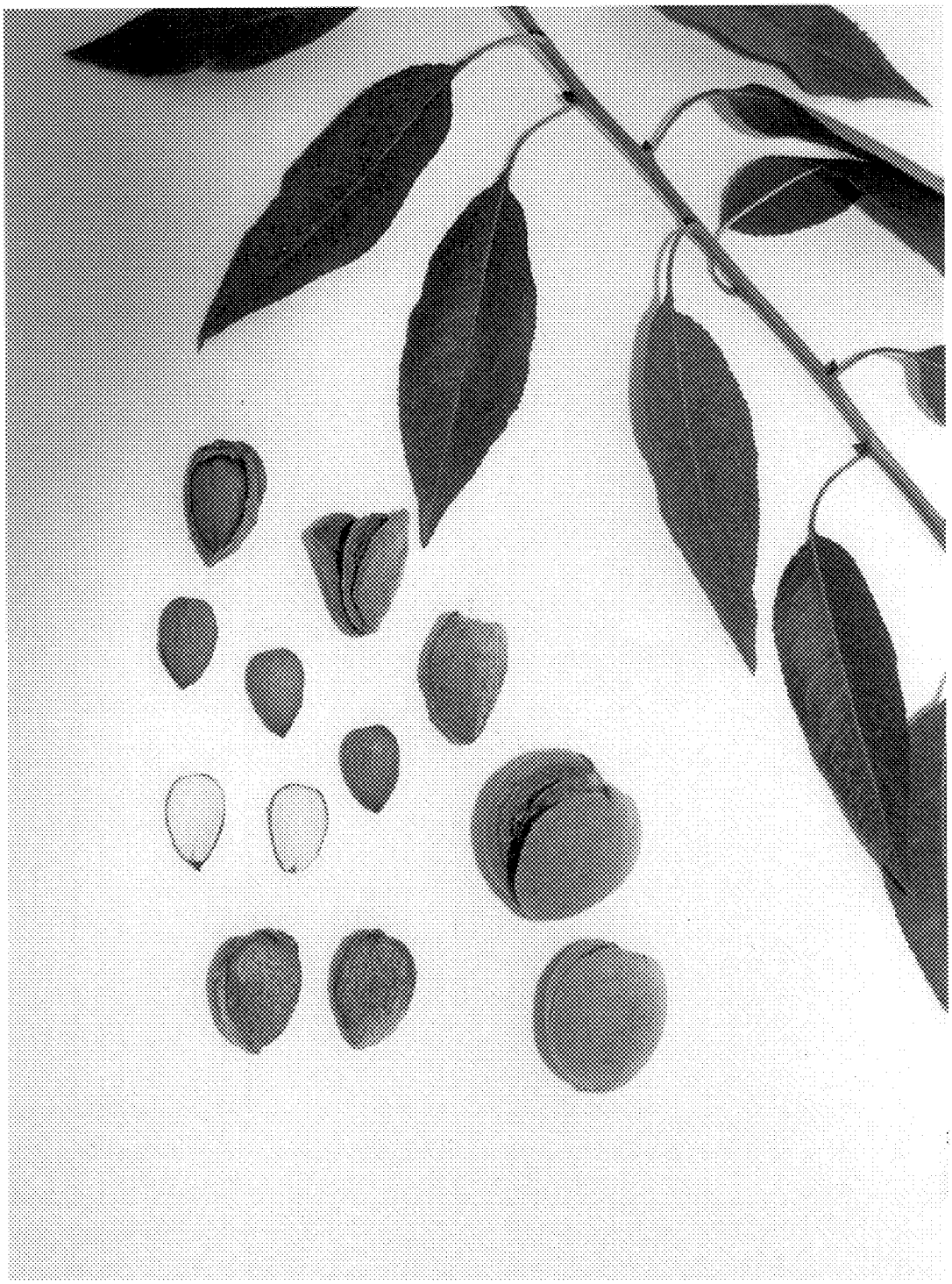

* * * * *